(12) United States Patent
Kurachi et al.

(10) Patent No.: US 6,857,316 B2
(45) Date of Patent: Feb. 22, 2005

(54) GAS SENSOR, GAS SENSOR INSTALLATION STRUCTURE, AND METHOD FOR INSTALLING GAS SENSOR

(75) Inventors: Hiroshi Kurachi, Nagakute-Gun (JP); Nobukazu Ikoma, Nagoya (JP); Sang Jae Lee, Ama-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 10/854,728

(22) Filed: May 26, 2004

(65) Prior Publication Data

US 2004/0216513 A1 Nov. 4, 2004

Related U.S. Application Data

(62) Division of application No. 10/396,633, filed on Mar. 25, 2003, now Pat. No. 6,796,175.

(30) Foreign Application Priority Data

Mar. 29, 2002 (JP) ........................................ 2002-095842

(51) Int. Cl.[7] ............................ G01N 7/00; G01D 11/24
(52) U.S. Cl. ........................... 73/431; 73/23.2; 73/31.05
(58) Field of Search ............................ 73/31.05, 23.2, 73/23.32, 431

(56) References Cited

U.S. PATENT DOCUMENTS

| | | | |
|---|---|---|---|
| 4,096,752 A | 6/1978 | Tonnelli | |
| 5,401,962 A | 3/1995 | Ferran | |
| 5,571,947 A | 11/1996 | Senn et al. | |
| 6,302,402 B1 | 10/2001 | Rynders et al. | |
| 6,673,224 B2 | 1/2004 | Shirai | |
| 6,796,175 B2 * | 9/2004 | Kurachi et al. | ............... 73/431 |

FOREIGN PATENT DOCUMENTS

| | | |
|---|---|---|
| JP | 05-232062 | 9/1993 |
| JP | 06-331596 | 12/1994 |
| JP | 08-278280 | 10/1996 |

* cited by examiner

Primary Examiner—Michael Cygan
(74) Attorney, Agent, or Firm—Burr & Brown

(57) ABSTRACT

A gas sensor includes a sensor element having a specific function, and a housing containing the sensor element therein and including a thread section, and a sealing surface which forms a sealing section together with an installation section at a position deeper than the thread section in a direction in which the sensor element is inserted. When the housing is screwed into the installation section, the release torque of the housing at 850° C. (1123 K) is 9 N·m or more, and an estimated value of a gap formed between the sealing surface and the installation section at 850° C. (1123 K) that is calculated according to a specific equation is 31 μm or less.

10 Claims, 3 Drawing Sheets

GAS SENSOR, GAS SENSOR INSTALLATION STRUCTURE, AND METHOD FOR INSTALLING GAS SENSOR

CROSS REFERENCE TO RELATED APPLICATIONS

This application is a division of U.S. application Ser. No. 10/396,633, filed Mar. 25, 2003, now U.S. Pat. No. 6,796,175 the entirety of which is incorporated herein by reference.

This application also claims the benefit of Japanese Application No. 2002-095842, filed Mar. 29, 2002, the entirety of which is incorporated herein by reference.

FIELD OF THE INVENTION

The present invention relates to a gas sensor, a gas sensor installation structure, and a method for installing gas sensor. More particularly, the present invention relates to a gas sensor which is rarely dislodged from an installation section, even if the gas sensor is installed in a vehicle or the like and is used under high temperature conditions, a gas sensor installation structure equipped with such a gas sensor, and a method for installing a gas sensor in such a manner.

BACKGROUND OF THE INVENTION

Various types of gas sensors are installed in the exhaust pipe (pipe) of a vehicle in order to detect a specific gas component ($NO_x$, for example) contained in exhaust gas. These types of gas sensors are generally installed in a specific pipe, such as the pipe 6 of the present invention shown in FIG. 1.

In the context of the present invention, a gas sensor 10 includes a sensor element 1 having a function of detecting $NO_x$ or the like, and a housing 5 which contains the sensor element 1 therein and includes a thread section 2 outside the housing and a sealing surface 4 which can form a sealing section 3 by coming in contact with a specific area of an installation section (boss 7). The boss 7 having a thread groove which can be screwed together with the thread section 2 of the housing 5 is secured to the pipe 6 in which the gas sensor 10 is installed. The gas sensor 10 is installed in the pipe 6 by screwing the housing 5 into the boss 7. As shown in FIG. 2, the sealing section 3 may be formed in a state in which a gasket 8 is disposed on the sealing surface 4 when installing the gas sensor 10.

As shown in FIG. 3, there may be a case where a rotating member (rotational hexagon 15), which can be rotated concentrically with the central axis of the housing 5, is disposed outside the housing 5, and the gas sensor 10 is installed so that the sealing surface 4 is pressed against the boss 7 by screwing the rotating member without rotating the housing 5. In the case of using the rotational hexagon 15, the sealing section 3 may also be formed in a state in which the gasket 8 is disposed on the sealing surface 4 in the same manner as shown in FIG. 2 (see FIG. 4).

Conventionally, in the case where the gas sensor is installed in the installation section by screwing the housing at an appropriate tightening torque, the installation area of the gas sensor may be subjected to high temperature when the temperature of the pipe is increased. For example, in the case where the gas sensor is installed in the exhaust pipe of a vehicle, the installation area of the gas sensor is subjected to a high temperature of 800–900° C. In this case, depending on the combination of the material for the boss and the material for the housing or gasket, a gap is easily formed at the sealing section under high temperature conditions due to the difference in coefficient of thermal expansion between the materials.

If a gap is formed at the sealing section, the tightening force of the screw is gradually decreased as the gap is increased. If the gas sensor is continuously used in a state in which the tightening force of the screw is decreased, the gas sensor may be dislodged from the pipe. In particular, since the possibility of dislodgement of the gas sensor is increased when used in an installation environment in which vibration is applied either continuously or intermittently, measures for eliminating such problems have been demanded.

The present invention has been achieved in view of the above-described problems in the conventional art. Accordingly, an object of the present invention is to provide a gas sensor which rarely allows the tightening force of the screw to be decreased even if the gas sensor is used under high temperature conditions when installed in a vehicle or the like, and is rarely dislodged from the pipe or the like in which the gas sensor is installed even if vibration is applied, a gas sensor installation structure equipped with the gas sensor, and a method for installing gas sensor.

SUMMARY OF THE INVENTION

According to the present invention, a gas sensor is provided, comprising a sensor element, which functions to detect a specific gas component, a housing containing the sensor element therein and having a sealing surface, a thread section which is adapted to be screwed into a specific installation section, and a sealing section formed between the sealing surface of the housing and a sealing surface of the installation section at a position deeper than the thread section in a direction in which the sensor element is inserted. When the housing is screwed into the installation section, the release torque of the housing at 850° C. (1123 K) is 9 N·m or more, and an estimated value $X_1$ of a gap formed between the sealing surface of the housing and the sealing surface of the installation section at 850° C. (1123 K), that is calculated according to the following equation (1), is 31 $\mu$m or less:

$$X_1(\mu m) = \{(L_1 \times \alpha_1) - (L_2 \times \alpha_2)\} \times 1123 \qquad (1);$$

wherein $X_1$ represents an estimated value ($\mu$m) of the gap, $L_1$ represents a length ($\mu$m) from the sealing surface of the installation section to a top end of the installation section, $L_2$ represents a length ($\mu$m) from the sealing surface of the housing to a top end of the thread section, $\alpha_1$ represents a coefficient of thermal expansion ($\times 10^{-6}$/° C.) of the installation section, and $\alpha_2$ represents a coefficient of thermal expansion ($\times 10^{-6}$/° C.) of the housing.

In the present invention, it is preferable that a gasket is provided in contact with the sealing surface of the housing and that an estimated value $X_2$ of the gap, that is calculated according to equation (2), is 31 $\mu$m or less:

$$X_2(\mu m) = \{(L_1 \times \alpha_1) - (L_2 \times \alpha_2) - (L_3 \times \alpha_3)\} \times 1123 \qquad (2);$$

wherein $X_2$ represents an estimated value ($\mu$m) of the gap, $L_1$ represents a length ($\mu$m) from the sealing surface of the installation section to a top end of the installation section, $L_2$ represents a length ($\mu$m) from the sealing surface of the housing to a top end of the thread section, $L_3$ represents a thickness ($\mu$m) of the gasket, $\alpha_1$ represents a coefficient of thermal expansion ($\times 10^{-6}$/° C.) of the installation section, $\alpha_2$ represents a coefficient of thermal expansion ($\times 10^{-6}$/° C.) of the housing, and $\alpha_3$ represents a coefficient of thermal expansion ($\times 10^{-6}$/° C.) of the gasket.

In the present invention, the material for the gasket is preferably at least one material selected from the group consisting of 430 SS, 304 SS, 310 SS, 316 SS, and 321 SS.

According to another aspect of the present invention, a gas sensor is provided, comprising a sensor element, which functions to detect a specific gas component, a housing containing the sensor element therein and having a sealing surface that forms a sealing section together with a sealing surface of an installation section at the front in the direction in which the sensor element is inserted, and a rotating member having a thread section formed on an outer surface thereof that is adapted to be screwed into the installation section and that can be rotated concentrically with respect to a central axis of the housing. When the gas sensor is installed in the installation section by screwing the rotating member into the installation section, the release torque of the rotating member at 850° C. (1123 K) is 9 N·m or more, and an estimated value $X_3$ of a gap formed between the sealing surface of the housing and the sealing surface of the installation section at 850° C. (1123 K), that is calculated according to the following equation (3), is 31 $\mu$m or less:

$$X_3(\mu m)=\{(L_1 \times \alpha_1)-(L_4 \times \alpha_4)-(L_5 \times \alpha_5)\} \times 1123 \qquad (3);$$

wherein $X_3$ represents an estimated value ($\mu$m) of the gap, $L_1$ represents a length ($\mu$m) from the sealing surface of the installation section to a top end of the installation section, $L_4$ represents a length ($\mu$m) from a bottom end to a top end of the thread section, $L_5$ represents a length ($\mu$m) from the sealing surface of the housing to the bottom end of the thread section, $\alpha_1$ represents a coefficient of thermal expansion ($\times 10^{-6}/°$ C.) of the installation section, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

In the present invention, it is preferable that a gasket is provided in contact with the sealing surface of the housing and that an estimated value $X_4$ of the gap, that is calculated according to equation (4), is 31 $\mu$m or less:

$$X_4(\mu m)=\{(L_1 \times \alpha_1)-(L_3 \times \alpha_3)-(L_4 \times \alpha_4)-(L_5 \times \alpha_5)\} \times 1123 \qquad (4);$$

wherein $X_4$ represents an estimated value ($\mu$m) of the gap, $L_1$ represents a length ($\mu$m) from the sealing surface of the installation section to a top end of the installation section, $L_3$ represents a thickness ($\mu$m) of the gasket, $L_4$ represents a length ($\mu$m) from a bottom end to a top end of the thread section, $L_5$ represents a length ($\mu$m) from the sealing surface of the housing to the bottom end of the thread section, $\alpha_1$, represents a coefficient of thermal expansion ($\times 10^{-6}/°$ C.) of the installation section, $\alpha_3$ represents a coefficient of thermal expansion ($\times 10^{-6}/°$ C.) of the gasket, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

In the present invention, the material for the gasket is preferably at least one material selected from the group consisting of 430 SS, 304 SS, 310 SS, 316 SS, and 321 SS. In the present invention, the material for the rotating member is preferably at least one material selected from the group consisting of 430 SS, 304 SS, 310 SS, 316 SS, and 321 SS. The material for the housing is preferably at least one material selected from the group consisting of 430 SS, 304 SS, 310 SS, 316 SS, and 321 SS.

According to another aspect of the present invention, a gas sensor installation structure is provided, including an installation section having a sealing surface and a gas sensor. The gas sensor comprises a sensor element, which functions to detect a specific gas component, a housing containing the sensor element therein and having a sealing surface, a thread section which is adapted to be screwed into the installation section, and a sealing section formed between the sealing surface of the housing and a sealing surface of the installation section at a position deeper than the thread section in a direction in which the sensor element is inserted. The gas sensor is installed by screwing the housing into the installation section. The release torque of the housing at 850° C. (1123 K) is 9 N·m or more, and an estimated value $X_5$ of a gap formed between the sealing surface of the housing and the sealing surface of the installation section at 850° C. (1123 K), that is calculated according to the following equation (5), is 31 $\mu$m or less:

$$X_5(\mu m)=\{(L_1 \times \alpha_1)-(L_2 \times \alpha_2)\} \times 1123 \qquad (5);$$

wherein $X_2$ represents an estimated value ($\mu$m) of the gap, $L_1$ represents a length ($\mu$m) from the sealing surface of the installation section to a top end of the installation section, $L_2$ represents a length ($\mu$m) from the sealing surface of the housing to a top end of the thread section, $\alpha_1$ represents a coefficient of thermal expansion ($\times 10^{-6}/°$ C.) of the installation section, and $\alpha_2$ represents a coefficient of thermal expansion ($\times 10^{-6}/°$ C.) of the housing.

In the present invention, it is preferable that the sealing section is formed through a gasket and that the estimated value $X_6$ of the gap, that is preferably calculated according to equation (6), is 31 $\mu$m or less:

$$X_6(\mu m)=\{(L_1 \times \alpha_1)-(L_2 \times \alpha_2)-(L_3 \times \alpha_3)\} \times 1123 \qquad (6);$$

wherein $X_6$ represents an estimated value ($\mu$m) of the gap, $L_1$ represents a length ($\mu$m) from the sealing surface of the installation section to a top end of the installation section, $L_2$ represents a length ($\mu$m) from the sealing surface of the housing to a top end of the thread section, $L_3$ represents a thickness ($\mu$m) of the gasket, $\alpha_1$ represents a coefficient of thermal expansion ($\times 10^{-6}/°$ C.) of the installation section, $\alpha_2$ represents a coefficient of thermal expansion ($\times 10^{-6}/°$ C.) of the housing, and $\alpha_3$ represents a coefficient of thermal expansion ($\times 10^{-6}/°$ C.) of the gasket.

In the present invention, the material for the gasket is preferably at least one material selected from the group consisting of 430 SS, 304 SS, 310 SS, 316 SS, and 321 SS.

According to another aspect of the present invention, a gas sensor installation structure is provided, including an installation section having a sealing surface and a gas sensor. The gas sensor comprises a sensor element, which functions to detect a specific gas component, a housing containing the sensor element therein and having a sealing surface which forms a sealing section together with the sealing surface of the installation section at the front in the direction in which the sensor element is inserted, and a rotating member having a thread section formed on an outer surface thereof that is adapted to be screwed into the installation section and that can be rotated concentrically with respect to a central axis of the housing. The gas sensor is installed in the installation section by screwing the rotating member into the installation section. The release torque of the rotating member at 850° C. (1123 K) is 9 N·m or more, and an estimated value $X_7$ of a gap formed between the sealing surface of the housing and the sealing surface of the installation section at 850° C. (1123 K), that is calculated according to the following equation (7), is 31 $\mu$m or less:

$$X_7(\mu m)=\{(L_1 \times \alpha_1)-(L_4 \times \alpha_4)-(L_5 \times \alpha_5)\} \times 1123 \qquad (7);$$

wherein $X_7$ represents an estimated value ($\mu$m) of the gap, $L_1$ represents a length ($\mu$m) from the sealing surface of the installation section to a top end of the installation section, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}$/° C.) of the installation section, $\alpha_4$ represents a coefficient of thermal expansion ($\times 10^{-6}$/° C.) of the rotating member, and $\alpha_5$ represents a coefficient of thermal expansion ($\times 10^{-6}$/° C.) of the housing.

In the present invention, it is preferable that the sealing section is formed through a gasket and an estimated value $X_8$ of the gap, that is calculated according to the following equation (8), is 31 μm or less:

$$X_8(\mu m) = \{(L_1 \times \alpha_1) - (L_3 \times \alpha_3) - (L_4 \times \alpha_4) - (L_5 \times \alpha_5)\} \times 1123 \quad (8);$$

wherein $X_8$ represents an estimated value (μm) of the gap, $L_1$ represents a length (μm) from the sealing surface of the installation section to a top end of the installation section, $L_3$ represents a thickness (μm) of the gasket, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}$/° C.) of the installation section, $\alpha_3$ represents a coefficient of thermal expansion ($\times 10^{-6}$/° C.) of the gasket, $\alpha_4$ represents a coefficient of thermal expansion ($\times 10^{-6}$/° C.) of the rotating member, and $\alpha_5$ represents a coefficient of thermal expansion ($\times 10^{-6}$/° C.) of the housing.

In the present invention, the material for the gasket is preferably at least one material selected from the group consisting of 430 SS, 304 SS, 310 SS, 316 SS, and 321 SS. In the present invention, the material for the rotating member is preferably at least one material selected from the group consisting of 430 SS, 304 SS, 310 SS, 316 SS, and 321 SS. The material for the housing is preferably at least one material selected from the group consisting of 430 SS, 304 SS, 310 SS, 316 SS, and 321 SS.

According to another aspect of the present invention, a method for installing a gas sensor is provided comprising the steps of providing an installation section having a sealing surface and providing a gas sensor which comprises a sensor element, which functions to detect a specific gas component, a housing containing the sensor element therein and having a sealing surface, a thread section which is adapted to be screwed into the installation section, and a sealing section formed between the sealing surface of the housing and the sealing surface of the installation section at a position deeper than the thread section in a direction in which the sensor element is inserted. The gas sensor is installed in the installation section by screwing the housing so that release torque of the housing at 850° C. (1123 K) is 9 N·m or more and an estimated value $X_9$ of a gap formed between the sealing surface of the housing and the sealing surface of the installation section at 850° C. (1123 K), that is calculated according to the following equation (9), is 31 μm or less:

$$X_9(\mu m) = \{(L_1 \times \alpha_1) - (L_2 \times \alpha_2)\} \times 1123 \quad (9);$$

wherein $X_9$ represents an estimated value (μm) of the gap, $L_1$ represents a length (μm) from the sealing surface of the installation section to a top end of the installation section, $L_2$ represents a length (μm) from the sealing surface of the housing to a top end of the thread section, $\alpha_1$ represents a coefficient of thermal expansion ($\times 10^{-6}$/° C.) of the installation section, and $\alpha_2$ represents a coefficient of thermal expansion ($\times 10^{-6}$/° C.) of the housing.

In the present invention, it is preferable that the sealing section is formed through a gasket and the housing is screwed so that an estimated value $X_{10}$ of the gap, that is calculated according to the following equation (10), is 31 μm or less:

$$X_{10}(\mu m) = \{(L_1 \times \alpha_1) - (L_2 \times \alpha_2) - (L_3 \times \alpha_3)\} \times 1123 \quad (10);$$

wherein $X_{10}$ represents an estimated value (μm) of the gap, $L_1$ represents a length (μm) from the sealing surface of the installation section to a top end of the installation section, $L_2$ represents a length (μm) from the sealing surface of the housing to a top end of the thread section, $L_3$ represents a thickness (μm) of the gasket, $\alpha_1$ represents a coefficient of thermal expansion ($\times 10^{-6}$/° C.) of the installation section, $\alpha_2$ represents a coefficient of thermal expansion ($\times 10^{-6}$/° C.) of the housing, and $\alpha_3$ represents a coefficient of thermal expansion ($\times 10^{-6}$/° C.) of the gasket.

According to another aspect of the present invention, a method for installing a gas sensor is provided, comprising the steps of providing an installation section having a sealing surface and providing a gas sensor, which comprises a sensor element which functions to detect a specific gas component, a housing containing the sensor element therein and having a sealing surface which forms a sealing section together with the sealing surface of the installation section at the front in a direction in which the sensor element is inserted, and a rotating member having a thread section formed on an outer surface thereof that is adapted to be screwed into the installation section and can be rotated concentrically with respect to a central axis of the housing. The gas sensor is installed in the installation section by screwing the rotating member so that release torque of the rotating member at 850° C. (1123 K) is 9 N·m or more and an estimated value $X_{11}$ of a gap formed between the sealing surface of the housing and the sealing surface of the installation section at 850° C. (1123 K), that is calculated according to the following equation (11), is 31 μm or less:

$$X_{11}(\mu m) = \{(L_1 \times \alpha_1) - (L_4 \times \alpha_4) - (L_5 \times \alpha_5)\} \times 1123 \quad (11);$$

wherein $X_{11}$ represents an estimated value (μm) of the gap, $L_1$ represents a length (μm) from the sealing surface of the installation section to a top end of the installation section, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}$/° C.) of the installation section, $\alpha_4$ represents a coefficient of thermal expansion ($\times 10^{-6}$/° C.) of the rotating member, and $\alpha_5$ represents a coefficient of thermal expansion ($\times 10^{-6}$/° C.) of the housing.

In the present invention, it is preferable that the sealing section is formed through a gasket and that the rotating member is screwed so that an estimated value $X_{12}$ of the gap, that is calculated according to the following equation (12), is 31 μm or less:

$$X_{12}(\mu m) = \{(L_1 \times \alpha_1) - (L_3 \times \alpha_3) - (L_4 \times \alpha_4) - (L_5 \times \alpha_5)\} \times 1123 \quad (12)$$

wherein $X_{12}$ represents an estimated value (μm) of the gap, $L_1$ represents a length (μm) from the sealing surface of the installation section to a top end of the installation section, $L_3$ represents a thickness (μm) of the gasket, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}$/° C.) of the installation section, $\alpha_3$ represents a coefficient of thermal expansion ($\times 10^{-6}$/° C.) of the gasket, $\alpha_4$ represents a coefficient of thermal expansion ($\times 10^{-6}$/° C.) of the rotating member, and α₅ represents a coefficient of thermal expansion (×10⁻⁶/° C.) of the housing.

DETAILED DESCRIPTION OF THE INVENTION

Embodiments of the present invention are described below. However, the present invention is not limited to these embodiments. Various modifications, improvements, and the like are possible within the scope of the present invention based on the knowledge of a person skilled in the art.

According to the present invention, a gas sensor is provided, comprising a sensor element, which functions to detect a specific gas component, a housing containing the sensor element therein and having a sealing surface and a thread section which is adapted to be screwed into a specific installation section. The sensor element also includes a sealing section formed between the sealing surface of the housing and a sealing surface of the installation section at a position deeper than the thread section in a direction in which the sensor element is inserted. When the housing is screwed into the installation section, the release torque of the housing at 850° C. (1123 K) is 9 N·m or more, and an estimated value $X_1$ of a gap formed between the sealing surface of the housing and the sealing surface of the installation section at 850° C. (1123 K), that is calculated according to the following equation (1), is 31 μm or less:

$$X_1(\mu m) = \{(L_1 \times \alpha_1) - (L_2 \times \alpha_2)\} \times 1123 \quad (1);$$

wherein $X_1$ represents an estimated value (μm) of the gap, $L_1$ represents a length (μm) from the sealing surface of the installation section to a top end of the installation section, $L_2$ represents a length (μm) from the sealing surface of the housing to a top end of the thread section, $\alpha_1$ represents a coefficient of thermal expansion (×10⁻⁶/° C.) of the installation section, and $\alpha_2$ represents a coefficient of thermal expansion (×10⁻⁶/° C.) of the housing.

Figure 1:
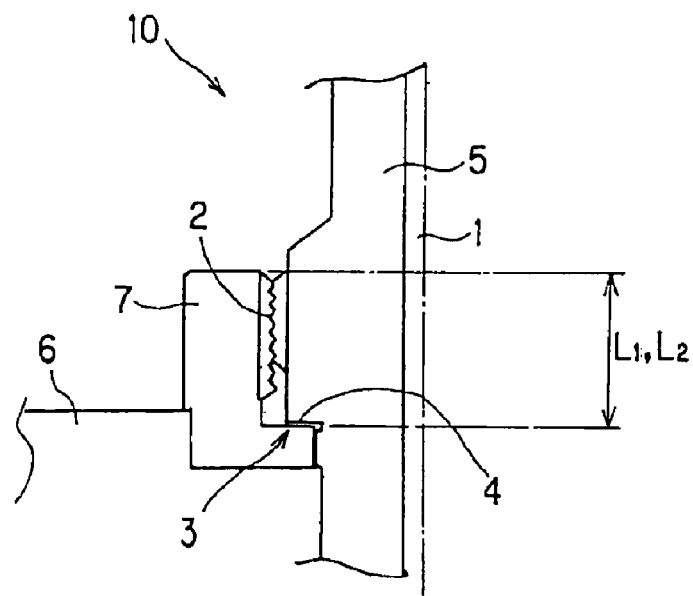
FIG. 1 is a partial cross-sectional view showing an embodiment of a gas sensor installation structure of the present invention.

The gas sensor of the present invention is described below in detail taking the gas sensor installation structure shown in FIG. 1 as an example. FIG. 1 illustrates a state in which the gas sensor 10 is installed in the pipe 6 by screwing the housing 5 into the boss 7 as described above. In the case where the relationship between the coefficient of thermal expansion ($\alpha_1$) of the boss 7, which is the installation section, and the coefficient of thermal expansion ($\alpha_2$) of the housing 5 is $\alpha_1 > \alpha_2$, a gap is formed between the sealing surface 4 of the housing 5 and the installation section (boss 7) at the sealing section 3 when the temperature of the pipe 6 is increased, whereby the tightening force of the screw is decreased. However, in the gas sensor of the present embodiment, since the release torque at 850° C. (1123 K) when the housing 5 is screwed into the installation section (boss 7) and the estimated value $X_1$ of the gap calculated according to the above equation (1) are specific values in the relationship between the coefficient of thermal expansion ($\alpha_1$) of the installation section and the length ($L_1$) between the sealing surface of the installation section and the top end of the installation section, the tightening force of the thread section 2 is maintained moderately. Therefore, the gas sensor of the present embodiment is rarely dislodged from the installation section (boss 7), even if the gas sensor is used in an installation environment in which vibration is applied either continuously or intermittently under high temperature conditions.

The term "release torque" used in the present invention means the torque necessary for dislodging the tightened product (gas sensor) from the installation section, or the torque necessary to cause the tightening force between the tightened product and the installation section to be lost, and is a measured value which is actually measured using a torque gauge.

In order to further reduce the possibility of dislodgement, it is preferable that the release torque at 850° C. (1123 K) when the housing is screwed into the installation section is 15 N·m or more, and that the estimated value $X_1$ of the gap calculated according to the above equation (1) is 20 μm or less. It is still more preferable that the release torque at 850° C. (1123 K) is 20 N·m or more and that the estimated value $X_1$ of the gap that is calculated according to the above equation (1) is 15 μm or less.

The upper limit of the release torque is not limited in the present invention. It is sufficient that the release torque is equal to or less than the torque during tightening from the viewpoint of preventing deformation of the thread section, seizing of the screw, and the like. The lower limit of the estimated value $X_1$ of the gap in the present invention is not limited. There may be a case where the estimated value $X_1$ of the gap is a negative value, since the estimated value $X_1$ is a theoretical value, and it is sufficient that the estimated value $X_1$ is about −10 μm or more.

Figure 2:
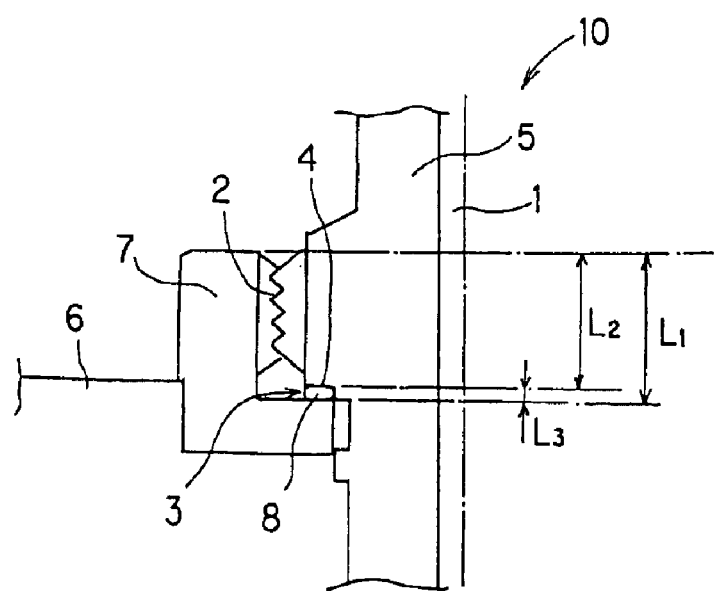
FIG. 2 is a partial cross-sectional view showing another embodiment of the gas sensor installation structure of the present invention.

The gas sensor of the present invention may have a configuration in which the gasket 8 is provided in contact with the sealing surface 4, as shown in FIG. 2. In this case, an estimated value $X_2$ of the gap can be calculated according to the following equation (2):

$$X_2(\mu m) = \{(L_1 \times \alpha_1) - (L_2 \times \alpha_2) - (L_3 \times \alpha_3)\} \times 1123 \quad (2);$$

wherein $X_2$ represents an estimated value (μm) of the gap, $L_1$ represents a length (μm) from the sealing surface of the installation section to a top end of the installation section, $L_2$ represents a length (μm) from the sealing surface of the housing to a top end of the thread section, $L_3$ represents a thickness (μm) of the gasket, $\alpha_1$ represents a coefficient of thermal expansion (×10⁻⁶/° C.) of the installation section, $\alpha_2$ represents a coefficient of thermal expansion (×10⁻⁶/° C.) of the housing, and $\alpha_3$ represents a coefficient of thermal expansion (×10⁻⁶/° C.) of the gasket.

According to another aspect of the present invention, a gas sensor is provided, comprising a sensor element, which functions to detect a specific gas component, a housing containing the sensor element therein and having a sealing surface which forms a sealing section together with a sealing surface of an installation section at the front in a direction in which the sensor element is inserted, and a rotating member having a thread section formed on an outer surface thereof that is adapted to be screwed into the installation section and that can be rotated concentrically with respect to a central axis of the housing. When the gas sensor is installed in the installation section by screwing the rotating member into the installation section, the release torque of the rotating member at 850° C. (1123 K) is 9 N·m or more, and an estimated value $X_3$ of a gap formed between the sealing surface of the housing and the sealing surface of the installation section at 850° C. (1123 K), that is calculated according to the following equation (3), is 31 μm or less:

$$X_3(\mu m) = \{(L_1 \times \alpha_1) - (L_4 \times \alpha_4) - (L_5 \times \alpha_5)\} \times 1123 \quad (3);$$

wherein $X_3$ represents an estimated value (μm) of the gap, $L_1$ represents a length (μm) from the sealing surface of the installation section to a top end of the installation section, $L_4$ represents a length (μm) from a bottom end to a top end of the thread section, $L_5$ represents a length from the sealing surface of the housing to the bottom end of the thread section (μm), $\alpha_1$ represents a coefficient of thermal expansion ($\times 10^{-6}/°$ C.) of the installation section, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

The gas sensor of the present invention is described below taking the gas sensor installation structure shown in FIG. 3 as an example.

As described above, FIG. 3 illustrates a state in which the rotating member (rotational hexagon 15) which can be rotated concentrically with respect to the central axis of the housing 5 is disposed outside the housing 5, and the gas sensor 10 is installed by screwing the rotating member so that the sealing surface 4 of the housing 5 is pressed against a sealing surface of the installation section (boss 7) without rotating the housing 5. In the case where the relationship between the coefficient of thermal expansion ($\alpha_1$) of the boss 7, which is the installation section, and the coefficients of thermal expansion ($\alpha_4$ and $\alpha_5$) of the housing 5 and the rotating member (rotational hexagon 15) is $\alpha_1 > \alpha_4$ and $\alpha_1 > \alpha_5$, a gap is formed between the sealing surface 4 of the housing 5 and the installation section (boss 7) at the sealing section 3 when the temperature of the pipe 6 is increased, whereby the tightening force of the screw is decreased. However, in the gas sensor of the present embodiment, since the value of the release torque at 850° C. (1123 K), when the rotational hexagon 15 (which is the rotating member) is screwed into the installation section (boss 7), and the estimated value $X_3$ of the gap that is calculated according to the above equation (3), are specific values in the relationship between the coefficient of thermal expansion ($\alpha_1$) of the installation section and the length ($L_1$) between the sealing surface of the installation section and the top end of the installation section, the tightening force of the thread section 2 is maintained moderately. Therefore, the gas sensor of the present embodiment is rarely dislodged from the installation section (boss 7) even if the gas sensor is used in an installation environment in which vibration is applied either continuously or intermittently under high temperature conditions.

In order to further reduce the possibility of dislodgement, it is preferable that the release torque at 850° C. (1123 K), when the rotating member is screwed into the installation section, is 15 N·m or more and that the estimated value $X_3$ of the gap that is calculated according to the above equation (3) is 20 μm or less. It is still more preferable that the release torque at 850° C. (1123 K) is 20 N·m or more and the estimated value $X_3$ of the gap that is calculated according to the above equation (3) is 15 μm or less.

In the present invention, the upper limit of the release torque is not limited. It is sufficient that the release torque is equal to or less than the torque during tightening from the viewpoint of preventing deformation of the thread section, seizing of the screw, and the like. The lower limit of the estimated value $X_1$ of the gap in the present invention is not limited. There may be a case where the estimated value $X_3$ of the gap is a negative value since the estimated value $X_3$ is a theoretical value, and it is sufficient that the estimated value $X_3$ is about −10 μm or more.

Figure 4:
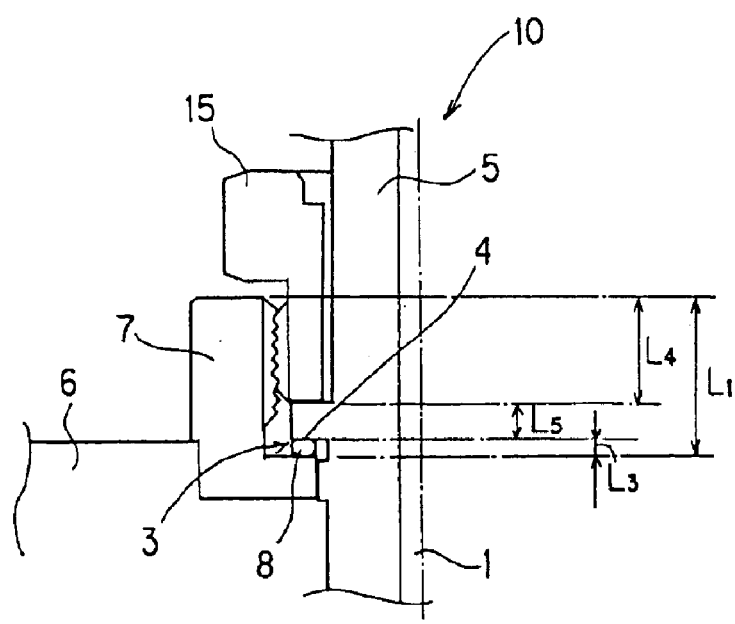
FIG. 4 is a partial cross-sectional view showing yet another embodiment of the gas sensor installation structure of the present invention.

In the present invention, a configuration in which the gasket 8 is provided in contact with the sealing surface 4, as shown in FIG. 4, may be employed. In this case, an estimated value $X_4$ of the gap can be calculated according to the following equation (4):

$$X_4(\mu m) = \{(L_1 \times \alpha_1) - (L_3 \times \alpha_3) - (L_4 \times \alpha_4) - (L_5 \times \alpha_5)\} \times 1123 \quad (4);$$

wherein $X_4$ represents an estimated value (μm) of the gap, $L_1$ represents a length (μm) from the sealing surface of the installation section to a top end of the installation section, $L_3$ represents a thickness (μm) of the gasket, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}/°$ C.) of the installation section, $\alpha_3$ represents a coefficient of thermal expansion ($\times 10^{-6}/°$ C.) of the gasket, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

In the present invention, the material for the gasket is preferably at least one material selected from the group consisting of 430 SS, 304 SS, 310 SS, 316 SS, and 321 SS. These materials can exhibit superior sealing properties at the sealing section and have excellent workability.

In the present invention, general-purpose materials are suitably used as the materials that make up the rotating member and the housing. As specific examples of the material for the rotating member, at least one material selected from the group consisting of 430 SS, 304 SS, 310 SS, 316 SS, and 321 SS is preferably used. As specific examples of the material for the housing, at least one material selected from the group consisting of 430 SS, 304 SS, 310 SS, 316 SS, and 321 SS is preferably used.

According to another aspect of the present invention, a gas sensor installation structure is provided, including an installation section having a sealing surface and a gas sensor. The gas sensor comprises a sensor element, which functions to detect a specific gas component, a housing containing the sensor element therein and having a sealing surface, a thread section which is adapted to be screwed into the installation section, and a sealing section formed between the sealing surface of the housing and the sealing surface of the installation section at a position deeper than the thread section in a direction in which the sensor element is inserted. The gas sensor is installed by screwing the housing into the installation section. The release torque of the housing at 850° C. (1123 K) of the housing is 9 N·m or more, and an estimated value $X_5$ of a gap formed between the sealing surface of the housing and the sealing surface of the installation section at 850° C. (1123 K), that is calculated according to the following equation (5), is 31 μm or less:

$$X_5(\mu m) = \{(L_1 \times \alpha_1) - (L_2 \times \alpha_2)\} \times 1123 \quad (5);$$

wherein $X_2$ represents an estimated value (μm) of the gap, $L_1$ represents a length (μm) from the sealing surface of the installation section to a top end of the installation section, $L_2$ represents a length ($\mu$m) from the sealing surface of the housing to a top end of the thread section, $\alpha_1$ represents a coefficient of thermal expansion ($\times 10^{-6}$/° C.) of the installation section, and $\alpha_2$ represents a coefficient of thermal expansion ($\times 10^{-6}$/° C.) of the housing.

The gas sensor installation structure of the present invention is described below taking the gas sensor installation structure shown in FIG. 1 as an example.

As described above, a gap is formed between the sealing surface 4 of the housing 5 and the installation section 7 at the sealing section 3 when the temperature of the pipe 6 is increased, whereby the tightening force of the screw is decreased. However, in the gas sensor installation structure of the present embodiment, since the release torque at 850° C. (1123 K) and the estimated value $X_5$ of the gap calculated according to the above equation (5) are specific values, the tightening force of the thread section 3 is maintained moderately. Therefore, even if the gas sensor installation structure of the present embodiment is used in an installation environment in which vibration is applied either continuously or intermittently under high temperature conditions, the gas sensor 10 is significantly rarely dislodged from the installation section (boss 7).

In order to further reduce the possibility of dislodgement, it is preferable that the release torque of the housing at 850° C. (1123 K) is 15 N·m or more and that the estimated value $X_5$ of the gap that is calculated according to the above equation (5) is 20 $\mu$m or less. It is still more preferable that the release torque at 850° C. (1123 K) is 20 N·m or more and that the estimated value $X_5$ of the gap that is calculated according to the above equation (5) is 15 $\mu$m or less.

In the present invention, the upper limit of the release torque is not limited. It is sufficient that the release torque is equal to or less than the torque during tightening from the viewpoint of preventing deformation of the thread section, seizing of the screw, and the like. The lower limit of the estimated value $X_1$ of the gap in the present invention is not limited. There may be a case where the estimated value $X_5$ of the gap is a negative value since the estimated value $X_5$ is a theoretical value, and it is sufficient that the estimated value $X_5$ is about $-10$ $\mu$m or more.

The gas sensor installation structure of the present invention may have a configuration in which the sealing section 3 is formed through the gasket 8, as shown in FIG. 2. In this case, an estimated value $X_6$ of the gap can be calculated according to the following equation (6):

$$X_6(\mu m) = \{(L_1 \times \alpha_1) - (L_2 \times \alpha_2) - (L_3 \times \alpha_3)\} \times 1123 \quad (6);$$

wherein $X_6$ represents an estimated value ($\mu$m) of the gap, $L_1$ represents a length ($\mu$m) from the sealing surface of the installation section to a top end of the installation section, $L_2$ represents a length ($\mu$m) from the sealing surface of the housing to a top end of the thread section, $L_3$ represents a thickness ($\mu$m) of the gasket, $\alpha_1$ represents a coefficient of thermal expansion ($\times 10^{-6}$/° C.) of the installation section, $\alpha_2$ represents a coefficient of thermal expansion ($\times 10^{-6}$/° C.) of the housing, and $\alpha_3$ represents a coefficient of thermal expansion ($\times 10^{-6}$/° C.) of the gasket.

In the present invention, the material for the gasket is preferably at least one material selected from the group consisting of 430 SS, 304 SS, 310 SS, 316 SS, and 321 SS. These materials can exhibit superior sealing properties at the sealing section and have excellent workability.

According to another aspect of the present invention, a gas sensor installation structure is provided, including an installation section having a sealing surface and a gas sensor. The gas sensor comprises a sensor element, which functions to detect a specific gas component, a housing containing the sensor element therein and having a sealing surface which forms a sealing section together with the sealing surface of the installation section at the front in a direction in which the sensor element is inserted, and a rotating member having a thread section formed on an outer surface thereof that is adapted to be screwed into the installation section and that can be rotated concentrically with respect to a central axis of the housing. The gas sensor is installed in the installation section by screwing the rotating member into the installation section. The release torque of the rotating member at 850° C. (1123 K) is 9 N·m or more, and an estimated value $X_7$ of a gap formed between the sealing surface of the housing and the sealing surface of the installation section at 850° C. (1123 K), that is calculated according to the following equation (7), is 31 $\mu$m or less:

$$X_7(\mu m) = \{(L_1 \times \alpha_1) - (L_4 \times \alpha_4) - (L_5 \times \alpha_5)\} \times 1123 \quad (7);$$

wherein $X_7$ represents an estimated value ($\mu$m) of the gap, $L_1$ represents a length ($\mu$m) from the sealing surface of the installation section to a top end of the installation section, $L_4$ represents a length ($\mu$m) from a bottom end to a top end of the thread section, $L_5$ represents a length ($\mu$m) from the sealing surface of the housing to the bottom end of the thread section, $\alpha_1$ represents a coefficient of thermal expansion ($\times 10^{-6}$/° C.) of the installation section, $\alpha_4$ represents a coefficient of thermal expansion ($\times 10^{-6}$/° C.) of the rotating member, and $\alpha_5$ represents a coefficient of thermal expansion ($\times 10^{-6}$/° C.) of the housing.

The gas sensor installation structure of the present invention is described below taking the gas sensor installation structure shown in FIG. 3 as an example.

Figure 3:
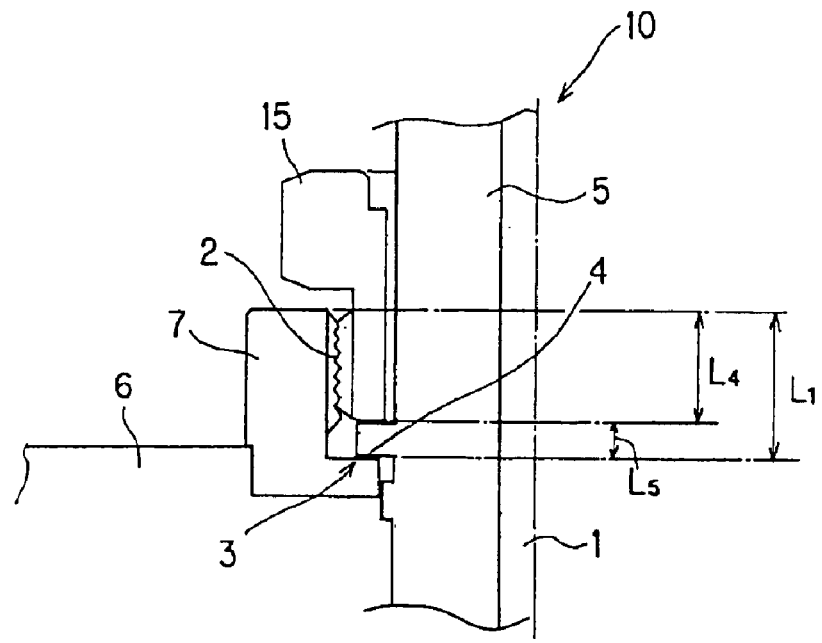
FIG. 3 is a partial cross-sectional view showing still another embodiment of the gas sensor installation structure of the present invention.

FIG. 3 illustrates a state in which the rotating member (rotational hexagon 15), which can be rotated concentrically with the center axis of the housing 5, is disposed outside the housing 5, and the gas sensor installation structure is formed by screwing the rotating member so that the sealing surface 4 is pressed against the boss 7 without rotating the housing 5. In the case where the relationship between the coefficient of thermal expansion ($\alpha_1$) of the boss 7, which is the installation section, and the coefficients of thermal expansion ($\alpha_4$ and $\alpha_5$) of the housing 5 and the rotating member (rotational hexagon 15) is $\alpha_1 > \alpha_4$ and $\alpha_1 > \alpha_5$, a gap is formed between the sealing surface 4 of the housing 5 and the installation section 7 at the sealing section 3 when the temperature of the pipe 6 is increased, whereby the tightening force of the screw is decreased. However, in the gas sensor installation structure of the present invention, since the release torque at 850° C. (1123 K) and the estimated value $X_7$ of the gap calculated according to the above equation (7) are specific values, the tightening force of the thread section 2 is maintained moderately. Therefore, even if the gas sensor installation structure of the present embodiment is used in an installation environment in which vibration is applied either continuously or intermittently under high temperature conditions, the gas sensor is significantly rarely dislodged from the installation section (boss 7).

In order to further reduce the possibility of dislodgement, it is preferable that the release torque of the rotating member at 850° C. (1123 K) is 15 N·m or more and the estimated value $X_7$ of the gap that is calculated according to the above equation (7) is 20 $\mu$m or less. It is still more preferable that the release torque of the rotating member at 850° C. (1123 K) is 20 N·m or more and the estimated value $X_7$ of the gap calculated according to the above equation (7) is 15 $\mu$m or less.

In the present invention, the upper limit of the release torque of the rotating member is not limited. It is sufficient that the release torque is equal to or less than the torque during tightening from the viewpoint of preventing deformation of the thread section, seizing of the screw, and the like. The lower limit of the estimated value $X_1$ of the gap in the present invention is not limited. There may be a case where the estimated value $X_7$ of the gap is a negative value since the estimated value $X_7$ is a theoretical value, and it is sufficient that the estimated value $X_7$ is about $-10$ µm or more.

The gas sensor installation structure of the present invention may have a configuration in which the sealing section 3 is formed through the gasket 8, as shown in FIG. 4. In this case, an estimated value $X_8$ of the gap can be calculated according to the following equation (8):

$$X_8(\mu m) = \{(L_1 \times \alpha_1) - (L_3 \times \alpha_3) - (L_4 \times \alpha_4) - (L_5 \times \alpha_5)\} \times 1123 \quad (8)$$

wherein $X_8$ represents an estimated value (µm) of the gap, $L_1$ represents a length (µm) from the sealing surface of the installation section to a top end of the installation section, $L_3$ represents a thickness (µm) of the gasket, $L_4$ represents a length (µm) from a bottom end to a top end of the thread section, $L_5$ represents a length (µm) from the sealing surface of the housing to the bottom end of the thread section, $\alpha_1$ represents a coefficient of thermal expansion ($\times 10^{-6}/°$ C.) of the installation section, $\alpha_3$ represents a coefficient of thermal expansion ($\times 10^{-6}/°$ C.) of the gasket, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

In this case, the material for the gasket is preferably at least one material selected from the group consisting of 430 SS, 304 SS, 310 SS, 316 SS, and 321 SS. These materials can exhibit superior sealing properties at the sealing section and have excellent workability.

In the present invention, general-purpose materials are suitably used as the materials for the rotating member and the housing. As the material for the rotating member, at least one material selected from the group consisting of 430 SS, 304 SS, 310 SS, 316 SS, and 321 SS is preferably used. As the material for the housing, at least one material selected from the group consisting of 430 SS, 304 SS, 310 SS, 316 SS, and 321 SS is preferably used.

A method for installing gas sensor of the present invention is described below. According to the present invention, a method for installing a gas sensor is provided, comprising the steps of providing an installation section having a sealing surface and providing a gas sensor. The gas sensor comprises a sensor element, which functions to detect a specific gas component, a housing containing the sensor element therein and having a sealing surface, a thread section which is adapted to be screwed into the installation section, and a sealing section formed between the sealing surface of the housing and the sealing surface of the installation section at a position deeper than the thread section in a direction in which the sensor element is inserted. The gas sensor is installed in the installation section by screwing the housing so that release torque of the housing at 850° C. (1123 K) is 9 N·m or more and an estimated value $X_9$ of a gap formed between the sealing surface of the housing and the sealing surface of the installation section at 850° C. (1123 K), that is calculated according to the following equation (9), is 31 µm or less:

$$X_9(\mu m) = \{(L_1 \times \alpha_1) - (L_2 \times \alpha_2)\} \times 1123 \quad (9);$$

wherein $X_9$ represents an estimated value (µm) of the gap, $L_1$ represents a length (µm) from the sealing surface of the installation section to a top end of the installation section, $L_2$ represents a length (µm) from the sealing surface of the housing to a top end of the thread section, $\alpha_1$ represents a coefficient of thermal expansion ($\times 10^{-6}/°$ C.) of the installation section, and $\alpha_2$ represents a coefficient of thermal expansion ($\times 10^{-6}/°$ C.) of the housing.

The method for installing gas sensor is described below taking the gas sensor installation structure shown in FIG. 1 as an example.

In the case where the relationship between the coefficient of thermal expansion ($\alpha_1$) of the boss 7, which is the installation section, and the coefficient of thermal expansion ($\alpha_2$) of the housing 5 is $\alpha_1 > \alpha_2$, a gap is formed between the sealing surface 4 of the housing 5 and the installation section 7 at the sealing section 3 when the temperature of the pipe 6 is increased, whereby the tightening force of the screw is decreased. However, in the method for installing gas sensor of the present invention, since the housing is screwed so that the release torque at 850° C. (1123 K) and the estimated value $X_9$ of the gap formed between the sealing surface 4 and the installation section (boss 7) at 850° C. (1123 K), that is calculated according to the above equation (9), are specific values, a gas sensor installation structure in which a moderate contact pressure is maintained in the sealing section 3 even at a high temperature of 800–900° C. can be obtained, for example. Therefore, a gas sensor installation structure in which the gas sensor 10 is significantly rarely dislodged from the installation section (boss 7), even if the gas sensor installation structure is used in an installation environment in which vibration is applied either continuously or intermittently under high temperatures conditions, can be provided.

In order to further reduce the possibility of dislodgement, it is preferable to screw the housing so that the release torque at 850° C. (1123 K) is 15 N·m or more and the estimated value $X_9$ of the gap, that is calculated according to the above equation (9), is 20 µm or less. It is still more preferable to screw the housing so that the release torque at 850° C. (1123 K) is 20 N·m or more and the estimated value $X_9$ of the gap calculated according to the above equation (9) is 15 µm or less.

In the present invention, the upper limit of the release torque is not limited. It is sufficient that the release torque is equal to or less than the torque during tightening from the viewpoint of preventing deformation of the thread section, seizing of the screw, and the like. The lower limit of the estimated value $X_1$ of the gap in the present invention is not limited. There may be a case where the estimated value $X_9$ of the gap is a negative value since the estimated value $X_9$ is a theoretical value, and it is sufficient that the estimated value $X_9$ is about $-10$ µm or more.

In the method for installing gas sensor of the present invention, the sealing section 3 may be formed through the gasket 8, as shown in FIG. 2. In this case, an estimated value $X_{10}$ of the gap can be calculated according to the following equation (10):

$$X_{10}(\mu m) = \{(L_1 \times \alpha_1) - (L_2 \times \alpha_2) - (L_3 \times \alpha_3)\} \times 1123 \quad (10);$$

wherein $X_{10}$ represents an estimated value (µm) of the gap, $L_1$ represents a length (µm) from the sealing surface of the installation section to a top end of the installation section, $L_2$ represents a length (µm) from the sealing surface of the housing to a top end of the thread section, $L_3$ represents a thickness (µm) of the gasket, $\alpha_1$ represents a coefficient of thermal expansion ($\times 10^{-6}/°$ C.) of the installation section, $\alpha_2$ represents a coefficient of thermal expansion ($\times 10^{-6}/°$ C.) of the housing, and $\alpha_3$ represents a coefficient of thermal expansion ($\times 10^{-6}/°$ C.) of the gasket.

According to another aspect of the present invention, a method for installing a gas sensor is provided, comprising the steps of providing an installation section having a sealing surface and providing a gas sensor. The gas sensor comprises a sensor element, which functions to detect a specific gas component, a housing containing the sensor element therein and having a sealing surface which forms a sealing section together with the sealing surface of the installation section at the front in a direction in which the sensor element is inserted, and a rotating member having a thread section formed on an outer surface thereof that is adapted to be screwed into the installation section and that can be rotated concentrically with respect to a central axis of the housing. The gas sensor is installed in the installation section by screwing the rotating member so that a release torque of the rotating member at 850° C. (1123 K) is 9 N·m or more and an estimated value $X_{11}$ of a gap formed between the sealing surface of the housing and the sealing surface of the installation section at 850° C. (1123 K), that is calculated according to the following equation (11), is 31 μm or less:

$$X_{11}(\mu m)=\{(L_1 \times \alpha_1)-(L_4 \times \alpha_4)-(L_5 \times \alpha_5)\} \times 1123 \qquad (11);$$

wherein $X_{11}$ represents an estimated value (μm) of the gap, $L_1$ represents a length (μm) from the sealing surface of the installation section to a top end of the installation section, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}/°$ C.) of the installation section, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

The method for installing gas sensor is described below taking the gas sensor installation structure shown in FIG. 3 as an example.

FIG. 3 illustrates a state in which the rotating member (rotational hexagon 15), which can be rotated concentrically with respect to the central axis of the housing 5, is disposed outside the housing 5, and the gas sensor installation structure is formed by screwing the rotating member so that the sealing surface 4 is pressed against the boss 7 without rotating the housing 5. In the case where the relationship between the coefficient of thermal expansion ($\alpha_1$) of the boss 7 which is the installation section and the coefficients of thermal expansion ($\alpha_4$ and $\alpha_5$) of the housing 5 and the rotating member (rotational hexagon 15) is $\alpha_1 > \alpha_4$ and $\alpha_1 > \alpha_5$, a gap is formed between the sealing surface 4 of the housing 5 and the installation section (boss 7) at the sealing section 3 when the temperature of the pipe 6 is increased in this state, whereby the tightening force of the thread section 3 is decreased.

However, in the method for installing gas sensor of the present invention, since the rotational hexagon 15 is screwed so that the release torque at 850° C. (1123 K) and the estimated value $X_{11}$ of the gap formed between the sealing surface 4 and the installation section (boss 7) at 850° C. (1123 K), that is calculated according to the above equation (11), are specific values, a gas sensor installation structure in which a moderate contact pressure is maintained in the sealing section 3 even at a high temperature of 800–900° C. can be obtained. Therefore, a gas sensor installation structure in which the gas sensor 10 is significantly rarely dislodged from the installation section (boss 7) even if the gas sensor installation structure is used in an installation environment in which vibration is applied either continuously or intermittently under high temperature conditions can be provided.

In order to further reduce the possibility of dislodgement, it is preferable to screw the rotating member so that the release torque at 850° C. (1123 K) is 15 N·m or more and the estimated value $X_{11}$ of the gap calculated according to the above equation (11) is 20 μm or less. It is still more preferable to screw the rotating member so that the release torque at 850° C. (1123 K) is 20 N·m or more and the estimated value $X_{11}$ of the gap calculated according to the above equation (11) is 15 μm or less.

In the present invention, the upper limit of the release torque is not limited. It is sufficient that the release torque is equal to or less than the torque during tightening from the viewpoint of preventing deformation of the thread section, seizing of the screw, and the like. The lower limit of the estimated value $X_{11}$ of the gap in the present invention is not limited. There may be a case where the estimated value $X_{11}$ of the gap is a negative value since the estimated value $X_{11}$ is a theoretical value. It is sufficient that the estimated value $X_{11}$ is about −10 μm or more.

In the method for installing gas sensor of the present invention, the sealing section 3 may be formed through the gasket 8, as shown in FIG. 4. In this case, an estimated value $X_{12}$ of the gap can be calculated according to the following equation (12):

$$X_{12}(\mu m)=\{(L_1 \times \alpha_1)-(L_3 \times \alpha_3)-(L_4 \times \alpha_4)-(L_5 \times \alpha_5)\} \times 1123 \qquad (12);$$

wherein $X_{12}$ represents an estimated value (μm) of the gap, $L_1$ represents a length (μm) from the sealing surface of the installation section to a top end of the installation section, $L_3$ represents a thickness (μm) of the gasket, $L_4$ represents a length (μm) from a bottom end to a top end of the thread section, $L_5$ represents a length (μm) from the sealing surface of the housing to the bottom end of the thread section, $\alpha_1$ represents a coefficient of thermal expansion ($\times 10^{-6}/°$ C.) of the installation section, $\alpha_3$ represents a coefficient of thermal expansion ($\times 10^{-6}/°$ C.) of the gasket, $\alpha_4$ represents a coefficient of thermal expansion ($\times 10^{-6}/°$ C.) of the rotating member, and $\alpha_5$ represents a coefficient of thermal expansion ($\times 10^{-6}/°$ C.) of the housing.

In the method for installing gas sensor of the present invention, general-purpose materials are suitably used as the materials for the gasket, the rotating member, and the housing. As the material for the gasket, at least one material selected from the group consisting of 430 SS, 304 SS, 310 SS, 316 SS, and 321 SS is preferably used. As the material for the rotating member, at least one material selected from the group consisting of 430 SS, 304 SS, 310 SS, 316 SS, and 321 SS is preferably used. As the material for the housing, at least one material selected from the group consisting of 430 SS, 304 SS, 310 SS, 316 SS, and 321 SS is preferably used.

EXAMPLES

The present invention is described below in more detail by examples. However, the present invention is not limited by these examples.

Figure 5:
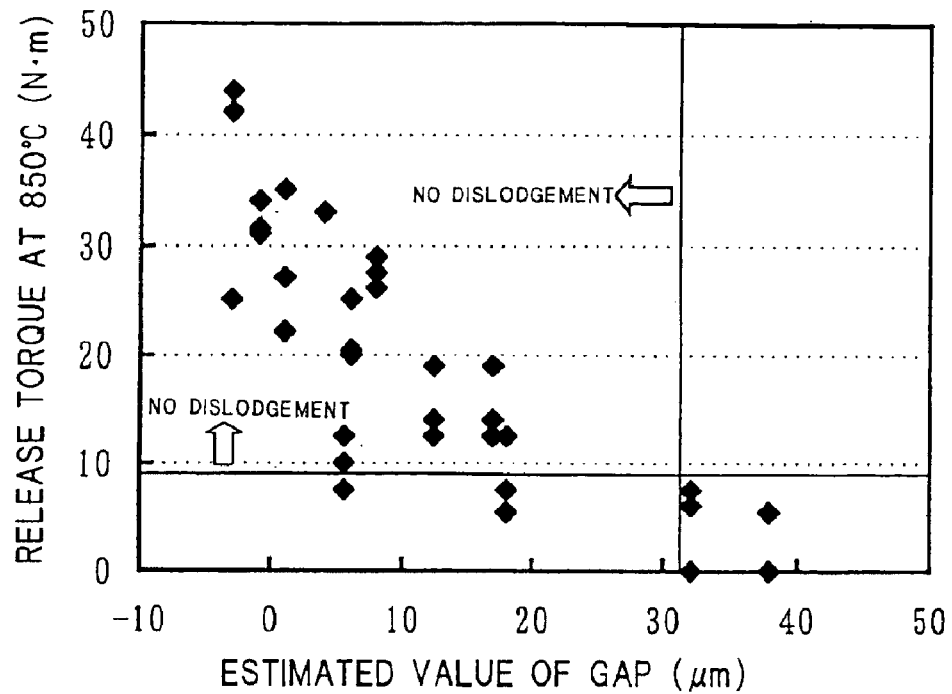
FIG. 5 is a graph showing the relation between dislodgement of a gas sensor and release torque (N·m) and an estimated value (μm) of a gap.

Relationship Between Dislodgement of Gas Sensor, Release Torque and Estimated Value of Gap:

Each constituent member formed of the materials shown in Table 1 was provided. The rotational hexagon was screwed into the boss at a tightening torque of 30 N·m or more at room temperature to obtain a gas sensor installation structure having a structure shown in FIG. 3 (samples Nos. 1–13). The length ($L_1$: mm) from the sealing surface to the top end of the boss (installation section) is shown in Table 1. The resulting gas sensor installation structures were allowed to stand under high temperature conditions of 850° C., and the release torque (N·m) of the rotational hexagon was measured. The estimated value ($\mu$m) of the gap formed between the sealing surface and the boss was calculated from the coefficient of thermal expansion ($\times 10^{-6}$/° C.) of the materials for each member and the lengths (mm) at each point ($L_1$ and $L_3$ to $L_5$). FIG. 5 is a graph in which the release torque (N·m) is plotted with respect to the resulting estimated values. The resulting gas sensor installation structures were subjected to a vibration test to confirm whether or not the gas sensor was dislodged. The results are shown in FIG. 5.

TABLE 1

| Sample No. | Material | | | | Length (L1: mm) |
|---|---|---|---|---|---|
| | Boss | Housing | Gasket | Rotational hexagon | |
| 1 | 316 SS | 430 SS | 430 SS | 430 SS | 9.5 |
| 2 | 316 SS | 430 SS | 430 SS | 304 SS | 9.5 |
| 3 | 304 SS | 430 SS | 430 SS | 316 SS | 9.5 |
| 4 | 316 SS | 430 SS | 430 SS | 430 SS | 11 |
| 5 | 304 SS | 430 SS | 430 SS | 304 SS | 9.5 |
| 6 | 316 SS | 430 SS | 430 SS | 304 SS | 9.5 |
| 7 | 316 SS | 430 SS | — | 304 SS | 9.5 |
| 8 | 316 SS | 430 SS | — | 304 SS | 9.5 |
| 9 | 316 SS | 430 SS | — | 304 SS | 9.5 |
| 10 | 304 SS | 430 SS | 430 SS | 304 SS | 9.5 |
| 11 | 304 SS | 430 SS | — | 304 SS | 9.5 |
| 12 | 304 SS | 430 SS | — | 304 SS | 9.5 |
| 13 | 304 SS | 430 SS | — | 304 SS | 9.5 |

As is clear from the results shown in FIG. 5, it was the gas sensor is not dislodged from the boss, which stallation section, when the release torque of the hexagon at 850° C. (1123 K) is 9 N·m or more and the value of the gap is 31 $\mu$m or less. Specifically, it was found that the gas sensor can be prevented from being dislodged in advance by appropriately selecting the materials and dimensions of the rotational hexagon, the gasket, and the housing for the material and dimensions of the boss, and appropriately controlling the tightening force (release torque) of the rotational hexagon.

Measurement of Release Torque:

The release torque of the rotational hexagon (rotating member) of the gas sensor installation structure was measured according to the following method. The gas sensor installation structure was formed by installing the gas sensor in the pipe. The gas sensor installation structure was then heated by allowing gas at 850° C. to flow through the pipe. After allowing the gas sensor installation structure to stand for two hours in this state, the release torque measured using a torque gauge was taken as the release torque (N·m) at 850° C.

Vibration Test:

The gas sensor installation structure thus obtained was subjected to a vibration test using test equipment and conditions shown in Table 2.

TABLE 2

| Test equipment | Propane burner |
|---|---|
| Gas temperature | 850° C. |
| Frequency | 50–250 Hz |
| Acceleration | 30–50 G |

Examples 1–4 and Comparative Examples 1–2

Figure 6:
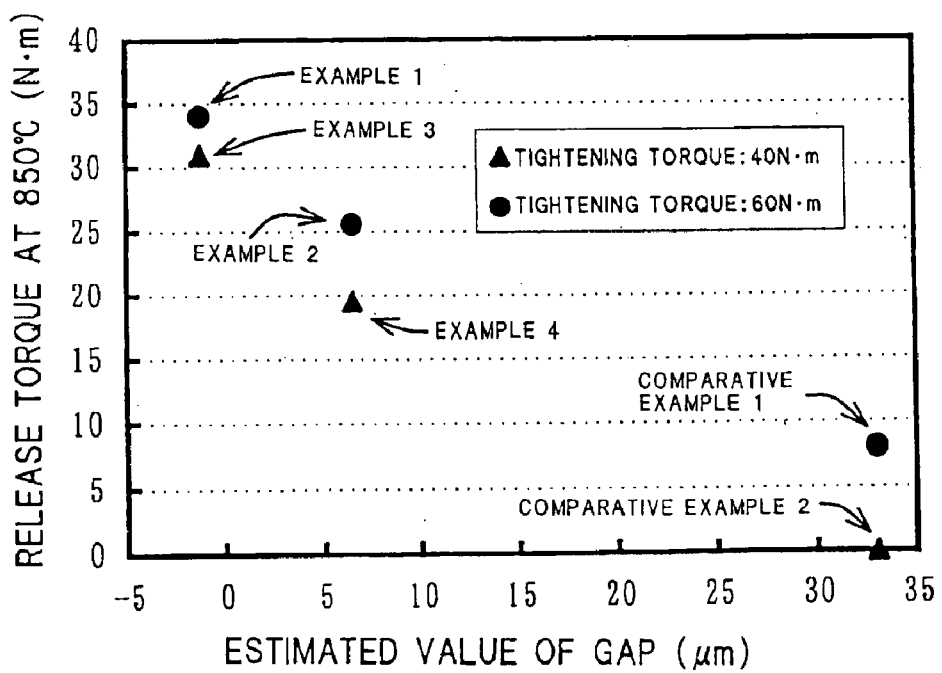
FIG. 6 is a graph in which release torque (N·m) at 850° C. is plotted with respect to an estimated value of a gap for each gas sensor installation structure obtained in examples.

Each constituent member formed of the materials shown in Table 3 was provided. The rotational hexagon was screwed into the boss at a tightening torque of 60 N·m or 40 N·m at room temperature to obtain a gas sensor installation structure having a structure shown in FIG. 3. The gas sensor installation structure thus obtained was allowed to stand under high temperature conditions of 850° C., and the release torque (N·m) of the rotational hexagon was measured. The estimated value ($\mu$m) of the gap formed between the sealing surface and the boss was calculated from the coefficients of thermal expansion ($\times 10^{-6}$/° C.) of the materials for each member and the lengths (mm) at each point ($L_1$ and $L_3$ to $L_5$). Table 3 shows the release torque (N·m) at 850° C. and the estimated value ($\mu$m) of the gap. FIG. 6 shows a graph in which the release torque (N·m) at 850° C. is plotted with respect to the estimated value of the gap.

TABLE 3

| | Material | | | Tightening torque | | | |
|---|---|---|---|---|---|---|---|
| | | | | 60 N · m | 40 N · m | Estimated | |
| | Rotational hexagon | Housing | Boss | Release torque at 850° C. (N · m) | | value of gap ($\mu$m) | Dislodgement |
| Example 1 | 304 SS | 430 SS | 304 SS | 34 | 30.9 | −1.2 | None |
| Example 2 | 304 SS | 430 SS | 316 SS | 25.4 | 19.7 | 6.4 | None |
| Example 3 | 304 SS | 430 SS | 304 SS | 34 | 30.9 | −1.2 | None |
| Example 4 | 304 SS | 430 SS | 316 SS | 25.4 | 19.7 | 6.4 | None |
| Comparative Example 1 | 430 SS | 430 SS | 316 SS | 8 | 0 | 32.8 | Dislodged |
| Comparative Example 2 | 430 SS | 430 SS | 316 SS | 8 | 0 | 32.8 | Dislodged |

The gas sensor installation structures thus obtained were subjected to the vibration test to confirm whether or not the gas sensor was dislodged. As a result, although the gas sensor was not dislodged in Examples 1–4, the gas sensor was dislodged in Comparative Examples 1 and 2 (see Table 3). Therefore, as shown in FIG. 6, it was confirmed that the gas sensor is not dislodged from the boss, which is the installation section, in the case where the release torque of the rotational hexagon at 850° C. (1123 K) is 9 N·m or more and the estimated value of the gap is 31 $\mu$m or less.

As described above, the gas sensor of the present invention rarely allows the tightening force of the screw to be decreased, even if the gas sensor is installed and used under high temperature conditions, and is rarely dislodged from the installation section, even if vibration is applied, since the release torque at a specific temperature in the case where the housing or the rotating member which is the constituent member is screwed into the installation section and the estimated value of the gap formed between the sealing surface of the housing and the installation section are specific values. The gas sensor installation structure of the present invention rarely allows the tightening force of the screw to be decreased even if the gas sensor installation structure is installed and used under high temperature conditions, and the gas sensor is rarely dislodged from the installation section even if vibration is applied, since the release torque of the housing or the rotating member at a specific temperature and the estimated value of the gap formed between the sealing surface and the installation section are specific values.

According to the method for installing gas sensor of the present invention, since the housing or the rotating member is screwed so that the release torque at a specific temperature and the estimated value of the gap formed between the sealing surface and the installation section are specific values, a gas sensor installation structure in which the gas sensor is significantly rarely dislodged from the installation section can be obtained.

What is claimed:

1. A gas sensor comprising a sensor element for detecting a specific gas component, a housing which contains said sensor element therein and has a sealing surface which forms a sealing section together with an installation section at the front in a direction in which said sensor element in inserted, and a rotating member which has a thread section which is formed outside said rotating member and is to be screwed into the installation section and can be rotated concentrically with respect to a central axis of said housing;

wherein when said gas sensor is installed in the installation section by screwing said rotating member into the installation section, a release torque of said rotating member at 850° C. (1123 K) is 9 N·m or more; and wherein an estimated value $X_3$ of a gap formed between said sealing surface of said housing and a sealing surface of the installation section at 850° C. (1123 K), that is calculated according to the following equation, is 31 µm or less:

$$X_3(\mu m) = \{(L_1 \times \alpha_1) - (L_4 \times \alpha_4) - (L_5 \times \alpha_5)\} \times 1123;$$

wherein $X_3$ represents an estimated value (µm) of the gap, $L_1$ represents a length (µm) from the sealing surface of the installation section to a top end of the installation section, $L_4$ represents a length (µm) from a bottom end to a top end of said thread section, $L_5$ represents a length (µm) from said sealing surface of said housing to the bottom end of said thread section, $\alpha_1$ represents a coefficient of thermal expansion ($\times 10^{-6}$/° C.) of the installation section, $\alpha_4$ represents a coefficient of thermal expansion ($\times 10^{-6}$/° C.) of said rotating member, and $\alpha_5$ represents a coefficient of thermal expansion ($\times 10^{-6}$/° C.) of said housing.

2. The gas sensor according to claim 1, wherein a gasket is provided in contact with said sealing surface of said housing and an estimated value $X_4$ of the gap, that is calculated according to the following equation, is 31 µm or less:

$$X_4(\mu m) = \{(L_1 \times \alpha_1) - (L_3 \times \alpha_3) - (L_4 \times \alpha_4) - (L_5 \times \alpha_5)\} \times 1123;$$

wherein $X_4$ represents an estimated value (µm) of the gap, $L_1$ represents a length (µm) from the sealing surface of the installation section to a top end of the installation section, $L_3$ represents a thickness (µm) of said gasket, $L_4$ represents a length (µm) from a bottom end to a top end of said thread section, $L_5$ represents a length (µm) from said sealing surface of said housing to the bottom end of said thread section, $\alpha_1$ represents a coefficient of thermal expansion ($\times 10^{-6}$/° C.) of the installation section, $\alpha_3$ represents a coefficient of thermal expansion ($\times 10^{-6}$/° C.) of said gasket, $\alpha_4$ represents a coefficient of thermal expansion ($\times 10^{-6}$/° C.) of said rotating member, and $\alpha_5$ represents a coefficient of thermal expansion ($\times 10^{-6}$/° C.) of said housing.

3. The gas sensor according to claim 2, wherein said gasket comprises at least one material selected from the group consisting of 430 SS, 304 SS, 310 SS, 316 SS, and 321 SS.

4. The gas sensor according to claim 1, wherein said rotating member comprises at least one material selected from the group consisting of 430 SS, 304 SS, 310 SS, 316 SS, and 321 SS.

5. A gas sensor installation structure comprising:

an installation section; and a gas sensor comprising a sensor element for detecting a specific gas component, a housing which contains said sensor element therein and has a sealing surface which forms a sealing section together with said installation section at the front in a direction in which said sensor element is inserted, and a rotating member which has a thread section which is formed outside said rotating member and is screwed into said installation section and can be rotated concentrically with respect to a central axis of said housing;

wherein said gas sensor is installed in said installation section by screwing said rotating member into said installation section;

wherein a release torque of said rotating member at 850° C. (1123 K) is 9 N·m or more; and wherein an estimated value $X_7$ of a gap formed between said sealing surface of said housing and a sealing surface of said installation section at 850° C. (1123 K), that is calculated according to the following equation, is 31 µm or less:

$$X_7(\mu m) = \{(L_1 \times \alpha_1) - (L_4 \times \alpha_4) - (L_5 \times \alpha_5)\} \times 1123;$$

wherein $X_7$ represents an estimated value (µm) of said gap, $L_1$ represents a length (µm) from said sealing surface of said installation section to a top end of said installation section, $L_4$ represents a length (µm) from a bottom end to a top end of said thread section, $L_5$ represents a length (µm) from said sealing surface of said housing to the bottom end of said thread section, $\alpha_1$ represents a coefficient of thermal expansion ($\times 10^{-6}$/° C.) of said installation section, $\alpha_4$ represents a coefficient of thermal expansion ($\times 10^{-6}$/° C.) of said rotating member, and $\alpha_5$ represents a coefficient of thermal expansion ($\times 10^{-6}$/° C.) of said housing.

6. The gas sensor installation structure according to claim 5, wherein said sealing section is formed through a gasket and an estimated value $X_8$ of said gap, that is calculated according to the following equation, 31 µm or less:

$$X_8(\mu m) = \{(L_1 \times \alpha_1) - (L_3 \times \alpha_3) - (L_4 \times \alpha_4) - (L_5 \times \alpha_5)\} \times 1123;$$

wherein $X_8$ represents an estimated value (µm) of said gap, $L_1$ represents a length (µm) from said sealing surface of said installation section to a top end of said installation section, $L_3$ represents a thickness (µm) of said gasket, $L_4$ represents a length (µm) from a bottom end to a top end of said thread section, $L_5$ represents a length (µm) from said sealing surface of said housing to the bottom end of said thread section, $\alpha_1$ represents a coefficient of thermal expansion ($\times 10^{-6}$/° C.) of said installation section, $\alpha_3$ represents a coefficient of thermal expansion ($\times 10^{-6}$/° C.) of said gasket, $\alpha_4$ represents a coefficient of thermal expansion ($\times 10^{-6}$/° C.)

of said rotating member, and $\alpha_5$ represents a coefficient of thermal expansion ($\times 10^{-6}/°$ C.) of said housing.

7. The gas sensor installation structure according to claim 6, wherein said gasket comprises at least one material selected from the group consisting of 430 SS, 304 SS, 310 SS, 316 SS, and 321 SS.

8. The gas sensor installation structure according to claim 5, wherein said rotating member comprises at least one material selected from the group consisting of 430 SS, 304 SS, 310 SS, 316 SS, and 321 SS.

9. A method for installing a gas sensor comprising the steps of:

providing an installation section having a sealing surface;

providing a gas sensor comprising a sensor element for detecting a specific gas component, a housing which contains said sensor element therein and has a sealing surface which forms a sealing section together with said installation section at the front in a direction in which said sensor element in inserted, and a rotating member which has a thread section which is formed outside said rotating member and is screwed into said installation section and can be rotated concentrically with respect to a central axis of said housing; and installing said gas sensor in said installation section by screwing said rotating member;

wherein a release torque of said rotating member at 850° C. (1123 K) is 9 N·m or more; and wherein an estimated value $X_{11}$ of a gap formed between said sealing surface of said housing and a sealing surface of said installation section at 850° C. (1123 K), that is calculated according to the following equation, is 31 μm or less:

$$X_{11}(\mu m) = \{(L_1 \times \alpha_1) - (L_4 \times \alpha_4) - (L_5 \times \alpha_5)\} \times 1123;$$

wherein $X_{11}$ represents an estimated value (μm) of said gap, $L_1$ represents a length (μm) from said sealing surface of said installation section to a top end of said installation section, $L_4$ represents a length (μm) from a bottom end to a top end of said thread section, $L_5$ represents a length (μm) from said sealing surface of said housing to the bottom end of said thread section, $\alpha_1$ represents a coefficient of thermal expansion ($\times 10^{-6}/°$ C.) of said installation section, $\alpha_4$ represents a coefficient of thermal expansion ($\times 10^{-6}/°$ C.) of said rotating member, and $\alpha_5$ represents a coefficient of thermal expansion ($\times 10^{-6}/°$ C.) of said housing.

10. The method for installing a gas sensor according to claim 9, wherein said sealing section is formed through a gasket and said rotating member is screwed in said installation step so that an estimated value $X_{12}$ of the gap, that is calculated according to the following equation, is 31 μm or less:

$$X_{12}(\mu m) = \{(L_1 \times \alpha_1) - (L_3 \times \alpha_3) - (L_4 \times \alpha_4) - (L_5 \times \alpha_5)\} \times 1123;$$

wherein $X_{12}$ represents an estimated value (μm) of said gap, $L_1$ represents a length (μm) from said sealing surface of said installation section to a top end of said installation section, $L_3$ represents a thickness (μm) of said gasket, $L_4$ represents a length (μm) from a bottom end to a top end of said thread section, $L_5$ represents a length (μm) from said sealing surface of said housing to the bottom end of said thread section, $\alpha_1$ represents a coefficient of thermal expansion ($\times 10^{-6}/°$ C.) of said installation section, $\alpha_3$ represents a coefficient of thermal expansion ($\times 10^{-6}/°$ C.) of the gasket, $\alpha_4$ represents a coefficient of thermal expansion ($\times 10^{-6}/°$ C.) of said rotating member, and $\alpha_5$ represents a coefficient of thermal expansion ($\times 10^{-6}/°$ C.) of said housing.

* * * * *